United States Patent [19]

Gebhardt

[11] Patent Number: 5,010,014

[45] Date of Patent: Apr. 23, 1991

[54] PERIFUSION APPARATUS FOR CULTURING LIVING CELLS AND PERIFUSION CULTURING PROCESS

[76] Inventor: Rolf Gebhardt, Dornäckerweg 13,, 7400 Tübingen 7, Fed. Rep. of Germany

[21] Appl. No.: 441,338

[22] Filed: Nov. 21, 1989

Related U.S. Application Data

[63] Continuation of Ser. No. 886, Jan. 6, 1987, abandoned.

[30] Foreign Application Priority Data

Jan. 10, 1986 [DE] Fed. Rep. of Germany ....... 3600487

[51] Int. Cl.$^5$ .............................................. C12M 1/14
[52] U.S. Cl. .................................. 435/310; 435/289; 435/290; 435/313
[58] Field of Search ........................... 435/283–286, 435/287, 290, 310, 313, 240.2, 241, 240, 813, 818, 809

[56] References Cited

U.S. PATENT DOCUMENTS

| | | | |
|---|---|---|---|
| 3,732,149 | 5/1973 | Santero | 435/290 |
| 3,843,454 | 10/1974 | Weiss | 435/285 |
| 4,172,013 | 10/1979 | Skoda et al. | 435/285 |
| 4,225,671 | 9/1980 | Puchinger et al. | 435/285 |
| 4,228,243 | 10/1980 | Iizuka | 435/285 |
| 4,748,124 | 5/1988 | Vogler | 435/285 |

FOREIGN PATENT DOCUMENTS 2624047 8/1977 Fed. Rep. of Germany .
3409501 10/1985 Fed. Rep. of Germany .

OTHER PUBLICATIONS

"Hormonal Interactions in the Control of Hepatic Enzyme Levels/Primary Cultures of Hepatocytes as Model Systems for Metabolic Regulation Research", Faculty of Chem. and Pharm. of the Eberhard-Karls University in Tubingen 1980, pp. 43–48.
Perifused Monolayer Cultures of Rat Hepatocytes as an Improved in Vitro System for Studies on Ureogenesis, by Rolf Gebhardt et al., 124, 1979, pp. 349–359.
Production of Anchorage-Dependent Cells-Problems and their Possible Solutions, Biotechnology and Bioengineering, vol. XXIII, pp. 2703–2716, 1981.
Perifusion System for Isolated Cells, Analytical Biochemistry, 112, pp. 117–127 (1981).

*Primary Examiner*—Thomas Wallen
*Attorney, Agent, or Firm*—Herbert Dubno

[57] ABSTRACT

In a perifusion apparatus for culturing living cells, the culture medium and the gas in the culture chamber are separated from one another by a gas-permeable wall, the liquid area being entirely filled with the culture medium. Gassing takes place through the gas-permeable wall. Several culture chambers can be interconnected as plug-in modules in such a way that common means can be used for liquid circulation, gassing and optionally thermizing.

5 Claims, 4 Drawing Sheets

PERIFUSION APPARATUS FOR CULTURING LIVING CELLS AND PERIFUSION CULTURING PROCESS

This is a continuation of co-pending application Ser. No. 07/000,886 filed on Jan. 6, 1987.

FIELD OF THE INVENTION

The invention relates to a perifusion apparatus for culturing or cultivating living cells with at least one culture chamber unit for receiving liquid culture medium and gas, at least one oxygenator for the culture medium, at least one hydraulic pump for the culture medium and at least one reservoir for the culture medium. The invention also relates to a process for perifusion culturing.

THE RELATED ART

A perifusion apparatus of this type is described in the dissertation of the Applicant "Hormonal Interactions in the Control of Hepatic Enzyme Levels/Primary Cultures of Hepatocytes as Model Systems for Metabolic Regulation Research", Faculty of Chemistry and Pharmacy of the Eberhard-Karls University in Tübingen, 1980, pp. 43–48, as well as in the publication by Rolf Gebhardt and Dieter Mecke "Perifused Monolayer Cultures of Rat Hepatocytes as an Improved In Vitro System for Studies on Ureogenesis" in Experimental Cell Research, 124, 1979, pp. 349–359. In these publications the culture chamber unit comprises a flat, rectangular dish with plugs on two facing ends and through which are passed the intake needles for the passage of the culture medium or gas. The chamber bottom is provided with several slides for culturing the cells. The culture chamber can be sealed with a cover and a seal. It is connected by means of hose lines to the reservoir, a peristaltic pump and an oxygenator. This perifusion apparatus is suitable for small scale scientific tests, but suffers from certain disadvantages referred to in the aforementioned publications.

OBJECTS OF THE INVENTION

The object of the present invention is to provide a perifusion apparatus, which permits the culturing of cells on a larger scale and under comparable conditions.

SUMMARY OF THE INVENTION

This object is achieved by having the area for the culture medium in the culture chamber unit separated by at least one gas-permeable wall from the space for the gas and the area for the culture medium constructed for a complete filling therewith during operation. Because of the separation of the culture chamber unit into a gas area and a liquid area by using a gas-permeable wall, handling of the perifusion apparatus is made much easier, because the liquid circuit and gas circuit are separate. The cell union always remains covered with culture medium in the case of a movement of the culture chamber unit.

The culture chamber unit is preferably flat or tabular, the gas-permeable partition running substantially parallel to a large flat side of the culture chamber unit. The gas-permeable partition is advantageously bacteria-tight, so that there is no risk of bacteria being transferred from the gaseous phase into the liquid phase. The gas-permeable wall is preferably substantially immovable. For this purpose the gas permeable wall can be constructed as a fundamentally flexible membrane, which is stiffened with a support structure. Thus, the area for the culture medium in the culture chamber unit has an invariable volume.

The perifusion apparatus is provided for a monolayer culture. Thus, the culture chamber advantageously contains at least one carrier, preferably a carrier plate for a monolayer culture and which is in particular parallel to the semipermeable wall. At least during the filling with culture medium, the culture chamber unit can be arranged in such a way that the inlet for the culture medium is at the bottom and the outlet at the top on the culture chamber unit, so that complete filling is ensured. Advantageously the culture chamber unit and gas permeable wall are substantially vertically positioned, which permits a space-saving installation of the perifusion apparatus. In the lower region of the culture chamber unit, a gas separator can be provided at the intake point for the culture medium to prevent the penetration of gas bubbles with culture medium into the culture chamber. This can be achieved in that in the lower region of the culture chamber unit, there is a feed duct for the culture medium and inlet points for the culture medium from the duct into the chamber are located below the top of the duct, so that the gas bubbles are collected on the upper wall of the duct and optionally removed. For feeding the culture medium into the culture chamber unit, there is preferably a plurality of inlets distributed over the entire chamber cross-section, which leads to a uniform, laminar flow. Thus, advantageously a feedline for the culture medium is passed along a lower narrow side and is connected to the chamber via a plurality of slots or holes and the feedline preferably slightly slopes from bottom to top.

It has been found that it is much easier to handle perifusion equipment if there are several and preferably at least five culture chambers, in each case in separate modules, which can be removed from the other modules and optionally from the reservoir for the culture medium and which can be connected thereto, particularly via detachable plug connections. The plug connections are preferably constructed as plug-in valves. Thus, it is no longer necessary to provide each culture chamber unit with separate feed lines. In fact the modules can be directly interconnected, so that one supply means or connection is sufficient for gassing, thermizing, a drive and/or the infeed of culture medium. A module has at least one culture chamber unit, but preferably also its own oxygenator and in particular its own circulating pump. This is particularly favourable for obtaining comparable conditions in the culture chambers of the individual modules. In this construction of the culture chamber units in the form of modules, the culture chambers are also advantageously subdivided into a gas area and a liquid area by means of a gas-permeable wall. The modules are preferably flat or tabular, so that they can be closely juxtaposed and in particular can be thermally coupled together with reciprocal contact. This also has an advantageous effect with regards to reproducible and comparable results. The modules can in each case be provided with a thermizing device, which is preferably located asymmetrically and flat on the outside of a module and more particularly on the side adjacent to the gas area. By placing the modules against one another, it is possible to ensure that a thermizing device also thermizes by thermal contact the side of the adjacent module not provided with such a device. Thermizing can be performed electrically. However, advantageously the thermizers have ducts for the passage of thermizing fluids. The final module of a row can them be provided on the free side with an additional thermizer, so that a symmetrical construction of the complete perifusion apparatus with respect to thermizing is achieved.

In the preferred embodiment the carriers, preferably carrier plates provided in the carrier for the culture medium, are removable. They can be removable as a single entity or subdivided into individual parts which are individually removable. Preferably on a narrow side, the culture chamber wall has a closable opening to permit the carriers to be removed. The narrow side is preferably the top in the operating position. It is possible to use different carriers, which are adapted, e.g. according to the nature of the material and the surface characteristics, to changing conditions of the particular cells, particularly with respect to the extracellular matrix and favorably influence the culturing conditions. The adhesion or growth of the cells on the carrier plate can be effected outside the culture chamber or within the latter in the horizontal position in the case of a stationary or very slowly flowing medium.

Since the chamber is subdivided into a gas area and a liquid area, the liquid layer formed from the culture medium can be kept very small over the cell union or carrier plate. Generally, a distance between carrier and in particular a carrier plate and the gas-permeable wall of approximately 0.8 to 1.2 and preferably approximately 1 mm is sufficient in general terms for the culture medium and the cell union. Thus, despite a large surface extension of the carrier for the cell union, the space for the culture medium in the culture chamber unit can be kept relatively small. In the case of a carrier plate with surface dimensions of approximately $12 \times 12$ cm and correspondingly dimensioned chambers, an available volume for the chamber medium of 10 to 20 cm$^3$, preferably approximately 15 cm$^3$ is sufficient. The gas-permeable wall is preferably arranged in the culture chamber unit in a detachable and, in particular, in an interchangeable manner. This is advantageous for cleaning and for using different gas-permeable walls.

The inventive perifusion culturing process of in particular human and animal cells, in which culture medium continuously flows round the cells in a culture chamber and saturated with a gaseous mixture prior to entering the culture chamber and also connected to the gaseous mixture within the culture chamber is characterized in that the gas exchange between the gaseous mixture and the culture medium within the culture chamber takes place through a gas-permeable wall separating the gas from the culture medium. The flow direction of gas and culture medium can be of a random nature, preference being given from a bottom to top flow at least during the time of filling the area for the culture medium. The area for the culture medium and in the culture chamber during operation of the perifusion apparatus is preferably free from a gaseous phase, apart from any additionally provided gas separators outside the carrier area. Thus, the cultured cells can always be kept covered with liquid, independently of the culture chamber position. The culture medium can also flow in laminar manner through the area of the chamber provided for it and substantially uniformly over the entire cross-section of the area between the membrane and the cell culture or its carrier. Culture medium and gas preferably have a countercurrent flow. Common reservoirs for the culture medium can be provided for several culture chamber units, but preferably separate reservoirs are provided for each unit. Since the culture chamber units are thermized, the culture medium, outside the culture chamber and e.g. in the reservoir, can be advantageously kept cooler than in the culture chamber unit, which is preferable for sterility reasons. Any gases passing out on heating of the culture medium are then separated prior to entry of the culture medium into the actual chamber. An exit of gases upstream of the chamber unit can be kept to a minimum by keeping the oxygenator and the chamber at the same temperature level.

The cells are cultured on the side or sides of the carrier facing the gas-permeable wall, so that a good gas exchange is ensured. The flow rate of the culture medium through the chamber is, inter alia, dependent on the adhesiveness of the cells on the carrier. In the case of a flow gap of approximately 1 mm between carrier and gas-permeable wall, the flow rate of the culture medium through the chamber can be kept at approximately 0.2 chamber volumes per minute.

BRIEF DESCRIPTION OF THE DRAWING

Further features and advantages of the invention will become more readily apparent from the following description of preferred embodiments, reference being made to the accompanying drawings in which.

SPECIFIC DESCRIPTION

Figure 1:
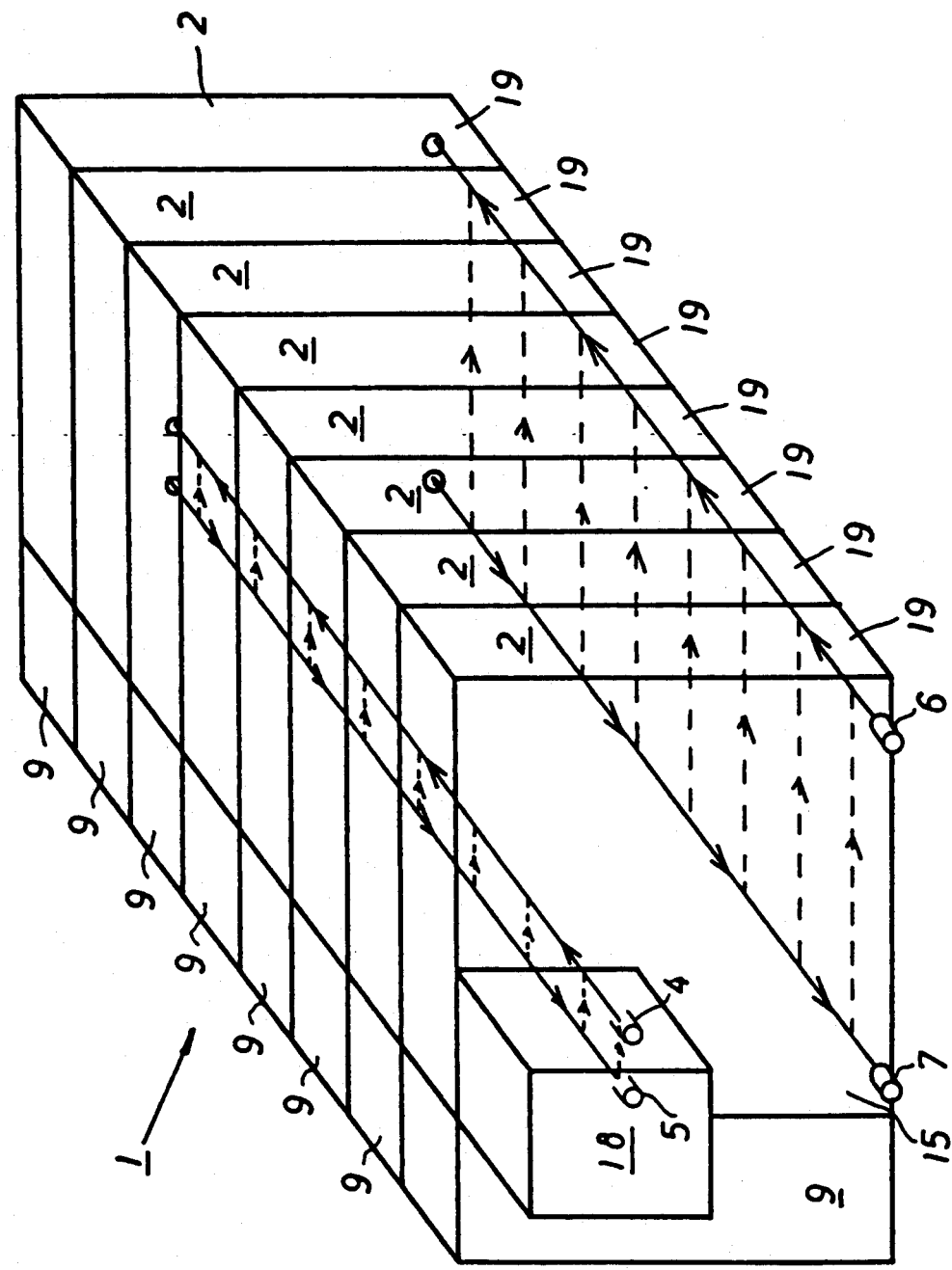
FIG. 1 is a diagrammatic perspective view of a preferred embodiment of the invention in modular form.
Figure 2:
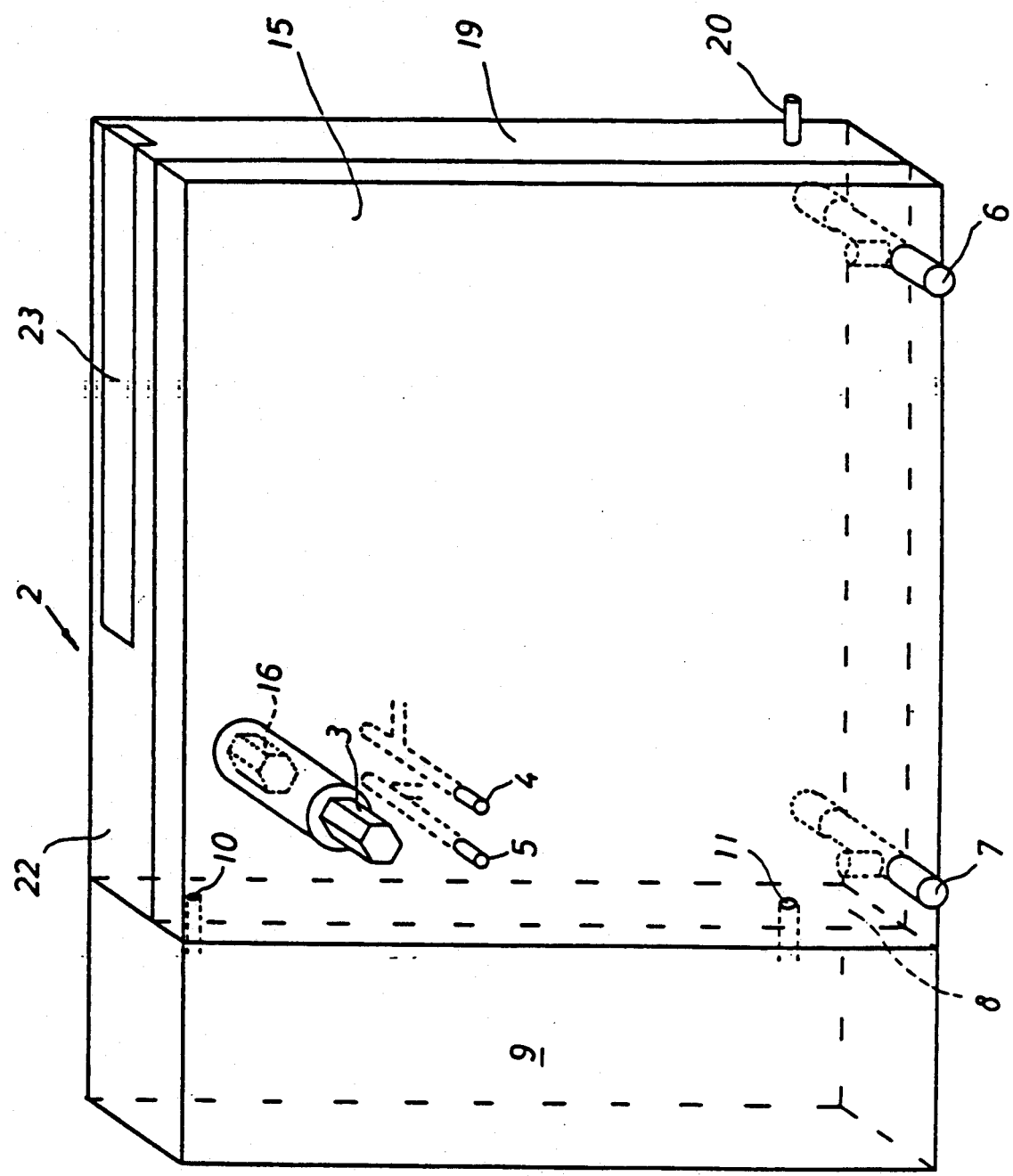
FIG. 2 is a perspective diagrammatic representation of a single module.

In the embodiment of the invention shown in the drawings, a perifusion apparatus 1 comprises eight modules 2, which are constructed in parallelopipedic manner and are interconnectable along large flat sides by means of plug connections 3, 4, 5, 6 and 7 (FIGS. 1 and 2).

Modules 2 are upright and engage with surface contact. Each module 2 is connected on one narrow side 8 to a separate reservoir 9 for culture medium by means of plug connections 10, 11, which serve as connecting lines for the culture medium. Each module 2 contains a peristaltic or hose pump 12, by means of which culture medium is sucked out of reservoir 9 and forced via an oxygenator 13 into a culture chamber unit 14. Hose pump 12 is driven mechanically by means of shafts with hexagonal plug-in pins 3, which project out of one flat side 15 of each module and engage in a corresponding recess 16 of the facing flat side 17 of the adjacent module 2. In a similar manner on the same side 15, plug-in pins 5, 6 project from gas lines and plug-in pins 7, 8 from liquid lines and corresponding receptacles are provided in the facing side 17. The plug connections for gases and liquids are provided with not shown plug-in valves, which are only open in the plugged-in state. The flow direction of the fluids is diagrammatically indicated by arrows in FIG. 1. A drive motor 18 is located on plug-in pin 3 on flat side 15 of first module 2 and synchronously drives all the hose pumps 12. On the narrow side 19 of module 2 directed away from reservoir 9, there is also an outlet 20 for culture medium at the bottom and this is used if there is merely a through-flow instead of a circulation of the culture medium through module 2. On the front flat side 15, each module 2 has a thermizing device or thermizer 21 extending over the entire side and which can be supplied with thermizing fluid by means of the plug connections 7, 8. Thermizers 21 also ensure that the desired temperature is maintained in the adjacent modules 2. On its rear side 17, the rearmost module 2 can be provided with an additional thermizer 21, so that all the modules can be thermized on both sides on their large flat sides 15, 17.

Figure 3:
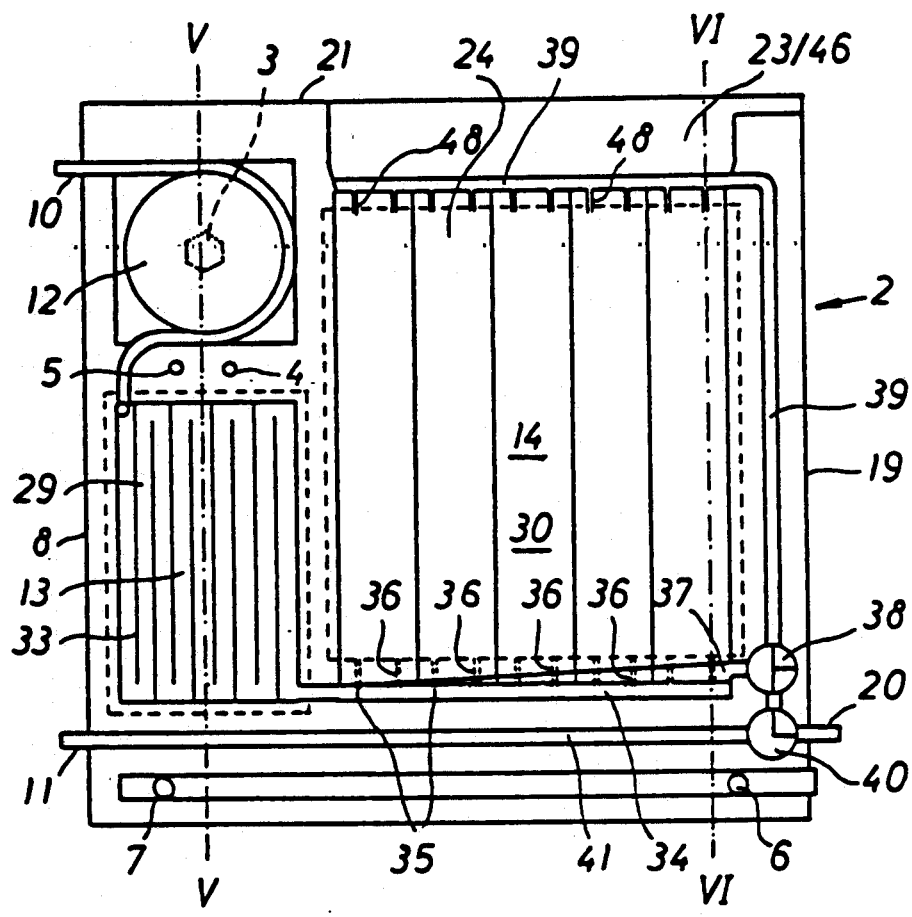
FIG. 3 is a vertical section through a module along line III—III according to FIGS. 5 and 6 on a reduced scale.
Figure 4:
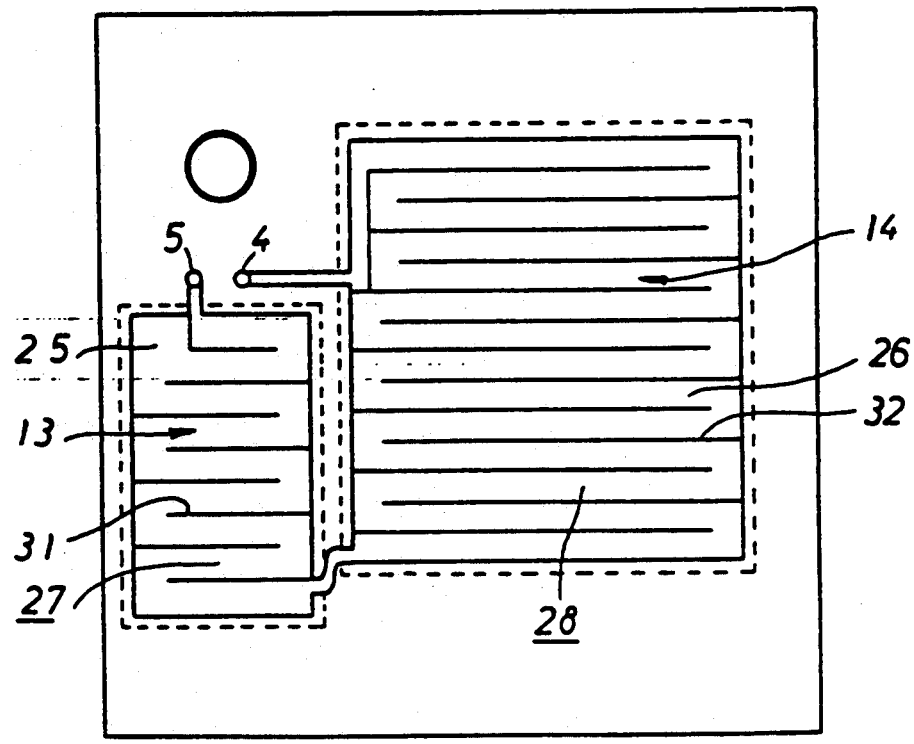
FIG. 4 is a section through the embodiment according to FIG. 3 along line IV—IV according to FIGS. 5 and 6 on a reduced scale.

FIG. 3 shows that module 2 contains pump 12, oxygenator 13 and chamber unit 14 in juxtaposed or superimposed form in a vertical plane. Not only oxygenator 13, but also culture chamber unit 14 are separated into an area 27 or 28 for the gas and an area 29 or 30 for the culture medium by gas-permeable membranes 25 or 26 parallel to the large lateral faces 15, 17. Membranes 25, 26 are made from flexible silicone material and are reinforced on the gas side with labyrinth-like, horizontally directed webs 31, 32, so that the volume for the gas or liquid areas is fixed. The webs simultaneously ensure that the flowing-along gas uniformly sweeps over the membrane. The gas is introduced through the plug connection 4 at right angles to the large flat sides 15, 17, flows in countercurrent manner to the culture medium firstly through the culture chamber unit 14 and then through the oxygenator 13 and leaves the module through plug connection 5. The culture medium flows from pump 12 initially into oxygenator 13 positioned alongside the culture chamber unit 14 and below pump 12 and in which it is deflected by vertical webs 33. The culture medium flows from the lower end of oxygenator 13 into the lower end of the culture chamber unit 14 along an upwardly sloping feed duct 34 extending over the entire width of chamber unit 14. Below its inner upper edge, the feed duct 13 has individual openings 35 through which the culture medium enters via short vertical lines 36 through the bottom 37 of liquid area 30 into the latter. Any gas bubbles which have separated from the culture medium before reaching the liquid chamber collect in the feed duct 34 above inlets 35, so that the feed duct serves as a gas separator. A three-way valve 38 is provided at end 37 of feed duct 34 and said valve is connected to the return line 39 for the culture medium from the upper end of the liquid area 30 of the chamber unit and is returned via a second three-way valve 40 either to the direct outlet 20 or via a recirculation return line 41 to plug connection 11 and therefore to reservoir 9. The air from the gas separator can be drawn off through three-way valve 38. In feed duct 34 and return line 39, the culture medium flows in the same direction, so that the culture medium always flows through the same path length up to return line 39 independently of whether it flows into liquid area 30 at the start of feed duct 34 or only at the end of said duct 34.

Figure 5:
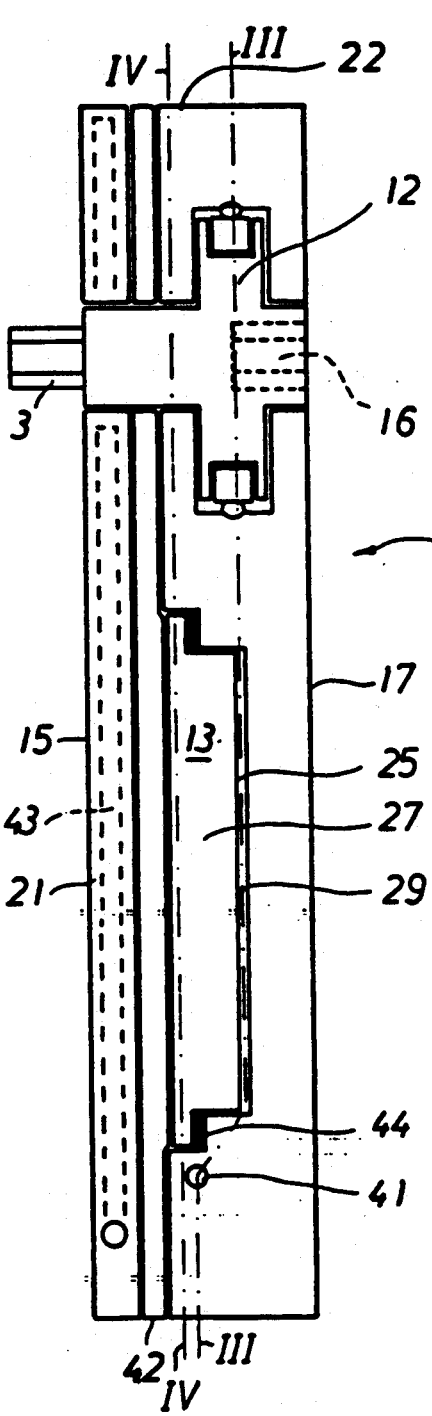
FIG. 5 is a section through the embodiment according to FIG. 3 along line V—V.
Figure 6:
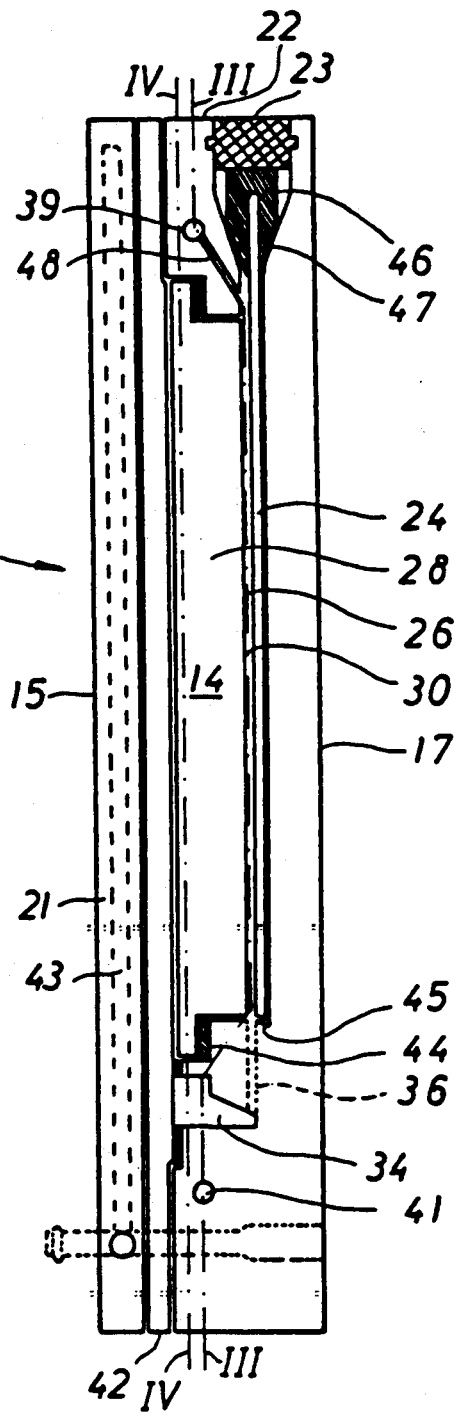
FIG. 6 is a section through the embodiment according to FIG. 3 along line VI—VI.

As can be gathered from FIGS. 5 and 6, module 2 is constructed in cross-section in multilayer form. To rear wall 17 is connected chamber unit 14 or oxygenator 13, on which is arranged a coverplate 42, which is solely perforated by pump 12 or the drive pins 3 thereof. Thermizer 21 is located above coverplate 42 and through it passes ducts 43 for the thermizing fluid. Compared with the liquid area 29, oxygenator 13 has a large gas area, which is separated by flat membrane 25 and a seal 44 from the parallel liquid area. The conditions correspond in the culture chamber unit 14, but therein the carrier plate 24 in liquid area 30 is at an internal spacing of approximately 1 mm from membrane 26. In the intermediate area the cells against which there is a laminar culture medium flow are cultured adhering in one layer form to carrier plate 24. Liquid area 30 and carrier plate 24 are subdivided into five vertical partial chambers or strips for performing parallel culturing operations. The adjustment of the carrier plate at the lower end takes place by means of a chamfer 45 by which the carrier plate is held on the rear wall of the chamber. At the upper end the carrier plate is provided with a weatherseal 46 pressed by means of cover 23 constructed as a slide into a cross-sectionally funnel-shaped introduction bevel 47 for the carrier plate 24. Below the introduction bevel 47, but above membrane 26, small ducts 48 branch from each partial chamber to return line 39, so that below the weatherseal the area once again serves as a gas separator and can be vented on removing the carrier plate. The area provided for the culture medium is therefore completely filled therewith in operation.

When operating the perifusion apparatus 1, it is possible to remove complete modules 2 or individual carrier plates 24, e.g. for checking cell growth or for taking samples, without impairing the other modules. It is possible to work under comparable conditions in the modules, so that more valid information is provided by the culturing results. Since the modules are constructed in block-like manner, they have bases, which greatly facilitates handling. In addition, the individual molded parts of the modules can be molded from plastic, e.g. by injection moulding and sealingly interconnected, which permits easy manufacture and cleaning.

I claim:
1. A perifusion culture apparatus comprising:
a horizontal assembly for vertical culturing modules each of flat rectangular configuration having opposite broad faces and comprising between said faces:
an oxygenation chamber subdivided by a gas permeable wall parallel to said faces into an oxygen compartment and a liquid culture medium compartment provided internally with means defining an upwardly extending meandering gas path and a downwardly extending meandering liquid path in counterflow to said gas path, respectively,
a culture chamber adjacent and coplanar with said oxygenation chamber and subdivided by a gas permeable wall parallel to said faces into a gas compartment and a culturing compartment, respectively,
a culture support removably received in said culturing compartment lying parallel to said faces and removable from said module with a culture thereon,
an inlet passage for an oxygen containing gas communicating with an upper part of said gas compartment, said gas compartment communicating at a bottom thereof with said oxygen compartment of said oxygenation chamber,
an outlet passage connected to an upper portion of said oxygen compartment of said oxygenation chamber,
a pump on said module connected to said liquid culture medium compartment of said oxygenation chamber for delivering a liquid culture medium to be oxygenated to said liquid culture medium compartment at an upper part thereof, means in said module for connecting a lower portion of said liquid culture medium compartment with said culturing compartment and for distributing an oxygenated culture medium all across a bottom of said culturing compartment, whereby said oxygenated medium passes upwardly therein and completely fills said culturing compartment, means for removing said culture medium communicating with said culturing compartment at a top thereof, and passages for a thermal fluid formed in said module;

a respective thermal control device connected with said passages for said thermal fluid coextensive with each of said modules and lying along and in surface contact with one of said faces, thereby controlling temperature in said chambers of the respective module;

means including plug connections for detachably interconnecting said pumps of the stacked modules and the passages thereof for jointly feeding said modules with oxygen containing gas and with said thermal fluid and for removing gas and said thermal fluid from the stack, whereby individual modules of said stack are removable therefrom and replaceable thereon; and a motor mounted on said stack for driving said pumps through the plug connections interconnecting said pumps.

2. The perifusion culture apparatus defined in claim 1 wherein the culture support of each culture chamber is spaced from the respective gas permeable wall of the culture chamber by a distance of 0.8 to 1.2 millimeters.

3. The perifusion culture apparatus defined in claim 1 wherein each of said modules is formed with a cover which can be opened to afford access to said culturing compartment.

4. The perifusion culture apparatus defined in claim 1 wherein said culture support is subdivided into a plurality of individual parallel strips.

5. The perifusion culture apparatus defined in claim 1 wherein said culture support has a surface structure configured to conform to an extracellular cell matrix of cells to be cultured.

* * * * *